US012011192B2

(12) United States Patent
Biedermann et al.

(10) Patent No.: US 12,011,192 B2
(45) Date of Patent: Jun. 18, 2024

(54) COUPLING ASSEMBLY FOR COUPLING A ROD TO A BONE ANCHORING ELEMENT, POLYAXIAL BONE ANCHORING DEVICE AND MODULAR STABILIZATION DEVICE

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE); Dimosthenis Dandanopoulos, VS-Schwenningen (DE); Achim Schünemann, VS-Mühlhausen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 22 days.

(21) Appl. No.: 17/324,524

(22) Filed: May 19, 2021

(65) Prior Publication Data

US 2021/0338287 A1    Nov. 4, 2021

Related U.S. Application Data

(63) Continuation of application No. 15/918,762, filed on Mar. 12, 2018, now Pat. No. 11,039,860, which is a
(Continued)

(30) Foreign Application Priority Data

Sep. 19, 2013    (EP) .................................. 13185176

(51) Int. Cl.
*A61B 17/70*    (2006.01)
(52) U.S. Cl.
CPC ...... *A61B 17/7032* (2013.01); *A61B 17/7002* (2013.01); *A61B 17/7035* (2013.01); *A61B 17/7037* (2013.01)

(58) Field of Classification Search
CPC ............................................. A61B 17/70–7046
See application file for complete search history.

(56) References Cited

U.S. PATENT DOCUMENTS 8,100,946 B2    1/2012  Strausbaugh et al.
9,358,047 B2 *  6/2016  Mishra ............... A61B 17/7082
(Continued)

FOREIGN PATENT DOCUMENTS

EP    1 935 358 A1    6/2008
EP    2 070 485 A1    6/2009
(Continued)

OTHER PUBLICATIONS

Extended European Search Report for European Application No. 13185176.8, European Search Report dated Feb. 5, 2014 and dated Feb. 12, 2014 (7 pgs.).

*Primary Examiner* — Eduardo C Robert
*Assistant Examiner* — Steven J Cotroneo
(74) *Attorney, Agent, or Firm* — Lewis Roca Rothgerber Christie LLP

(57) ABSTRACT

A coupling assembly for coupling a rod to a bone anchoring element, and including a receiving part having a first end, a second end, and an accommodation space having an opening at the second end for inserting a head of the bone anchoring element, a pressure element insertable from the first end, positionable in the accommodation space, and configured to hold the head, the pressure element having at least one spring portion extending circumferentially around the pressure element and being radially compressible, and a rod receiving element separable from the pressure element, wherein in a first position, the spring portion is configured to engage an engagement structure at an inner wall of the receiving part to prevent movement of the pressure element towards the first end, and wherein the rod receiving element
(Continued)

is configured to move the pressure element from the first position towards the second end.

26 Claims, 12 Drawing Sheets

Related U.S. Application Data continuation of application No. 14/490,569, filed on Sep. 18, 2014, now Pat. No. 9,943,338.

(60) Provisional application No. 61/879,916, filed on Sep. 19, 2013.

(56) References Cited

U.S. PATENT DOCUMENTS

| | | | | |
|---|---|---|---|---|
| 2004/0225289 A1* | 11/2004 | Biedermann | ...... | A61B 17/8605 606/279 |
| 2005/0216003 A1* | 9/2005 | Biedermann | ...... | A61B 17/7035 606/279 |
| 2007/0055241 A1* | 3/2007 | Matthis | ...... | A61B 17/7032 606/267 |
| 2007/0093826 A1* | 4/2007 | Hawkes | ...... | A61B 17/7037 606/279 |
| 2007/0093904 A1 | 4/2007 | Biedermann et al. | | |
| 2007/0118123 A1* | 5/2007 | Strausbaugh | ...... | A61B 17/7032 606/272 |
| 2008/0161931 A1 | 7/2008 | Perez-Cruet et al. | | |
| 2008/0200956 A1 | 8/2008 | Beckwith et al. | | |
| 2010/0145394 A1* | 6/2010 | Harvey | ...... | A61B 17/8685 606/305 |
| 2010/0152787 A1* | 6/2010 | Walsh | ...... | A61B 17/7037 606/305 |
| 2010/0160980 A1 | 6/2010 | Walsh et al. | | |
| 2010/0234902 A1 | 9/2010 | Biedermann et al. | | |
| 2011/0152949 A1* | 6/2011 | Biedermann | ...... | A61B 17/7037 606/305 |
| 2012/0059426 A1* | 3/2012 | Jackson | ...... | A61B 17/7076 606/300 |
| 2012/0277806 A1* | 11/2012 | Smith | ...... | A61B 17/7032 606/308 |
| 2013/0046350 A1 | 2/2013 | Jackson et al. | | |
| 2014/0142634 A1* | 5/2014 | Schlaepfer | ...... | A61B 17/704 29/428 |
| 2014/0228890 A1 | 8/2014 | Raju et al. | | |
| 2014/0343617 A1* | 11/2014 | Hannen | ...... | A61B 17/8605 606/306 |
| 2015/0045835 A1 | 2/2015 | Kim | | |

FOREIGN PATENT DOCUMENTS

| | | |
|---|---|---|
| JP | 2008-155028 A | 7/2008 |
| JP | 2009-142655 A | 7/2009 |
| WO | WO 2012/064360 A1 | 5/2012 |

* cited by examiner

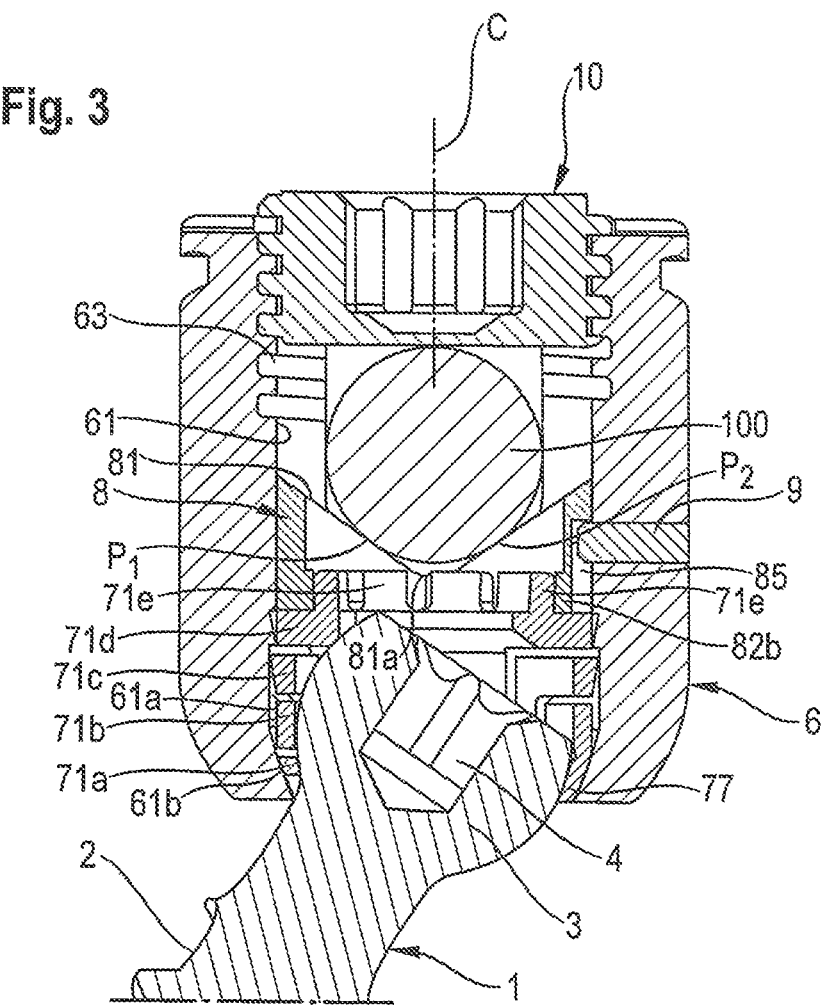

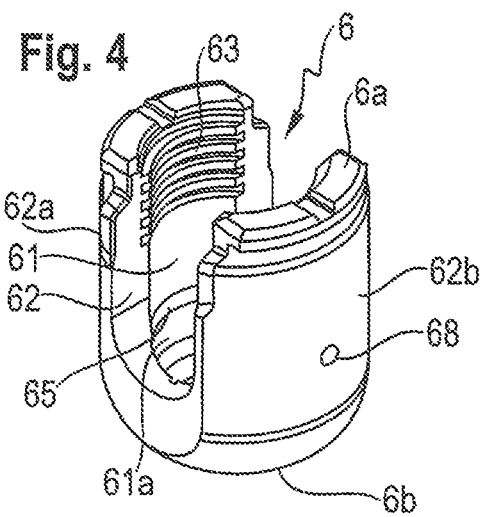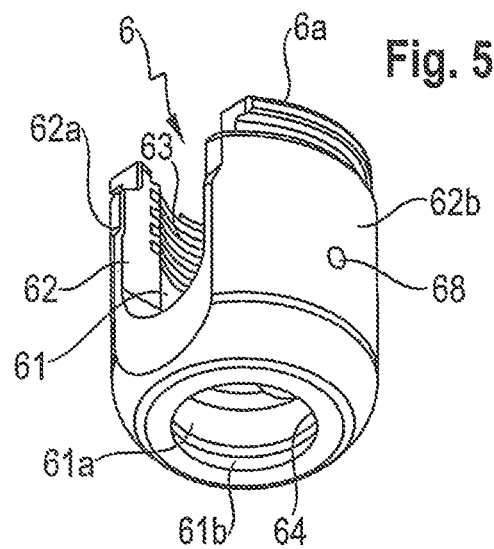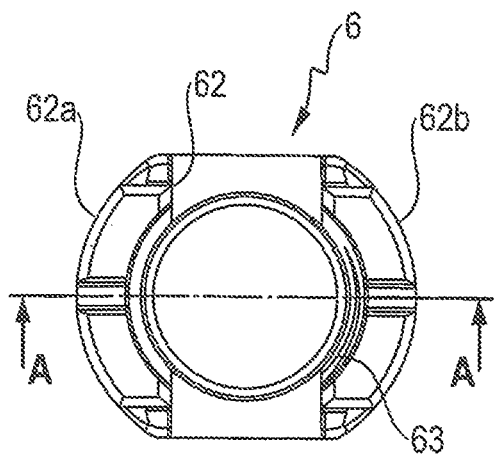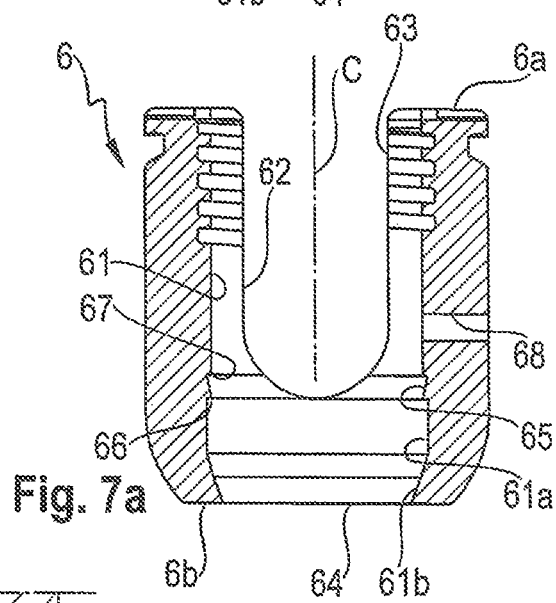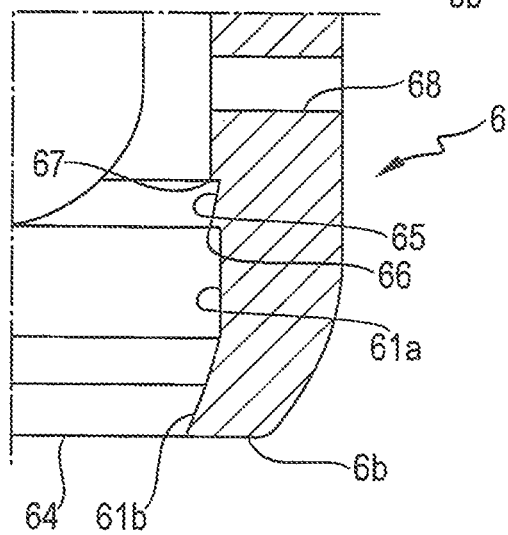

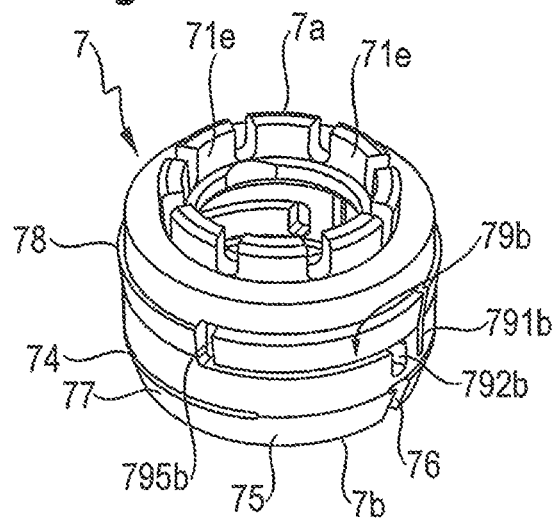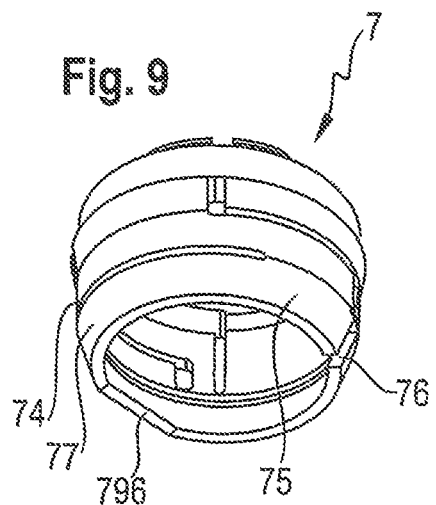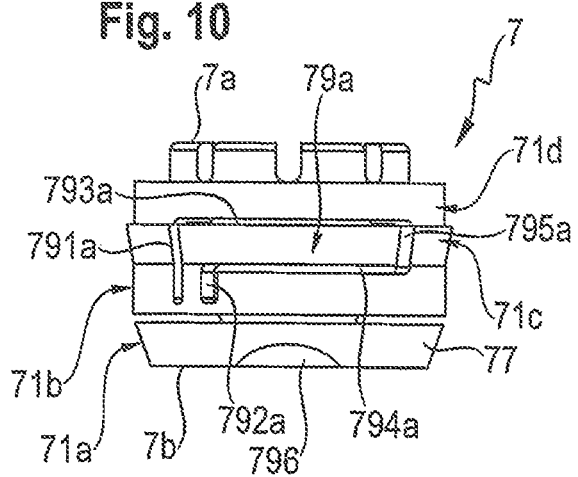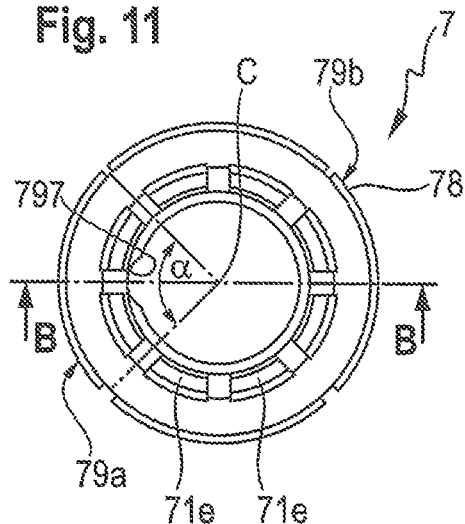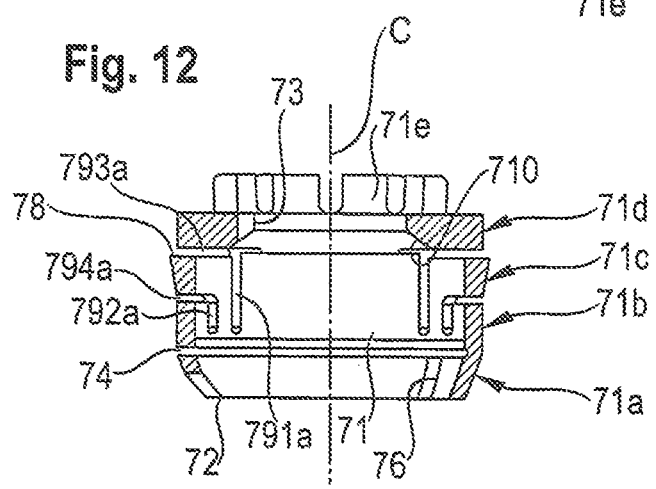

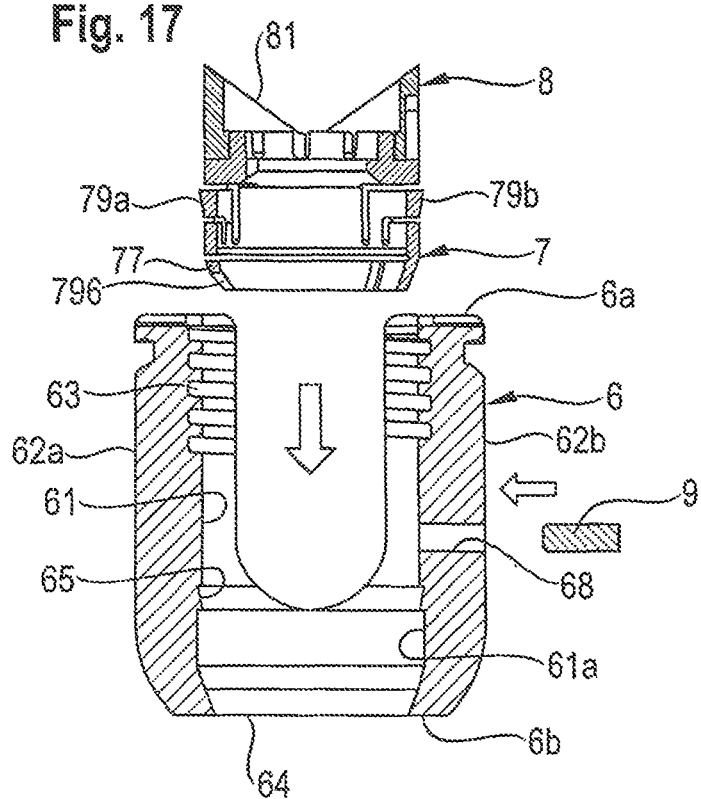
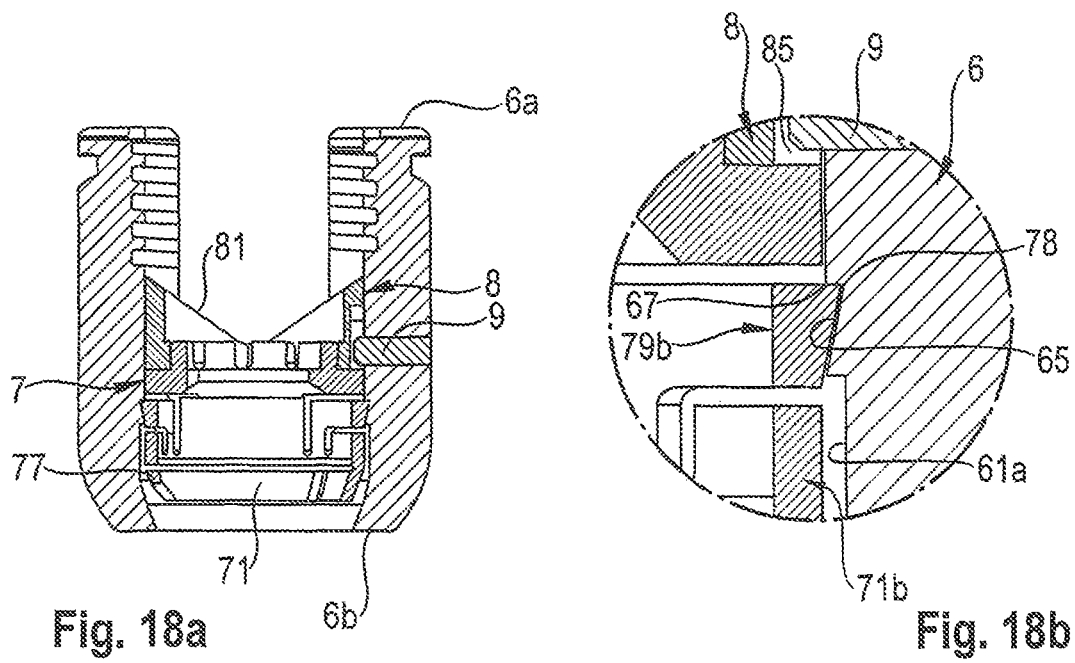
Fig. 17
Fig. 18a  Fig. 18b

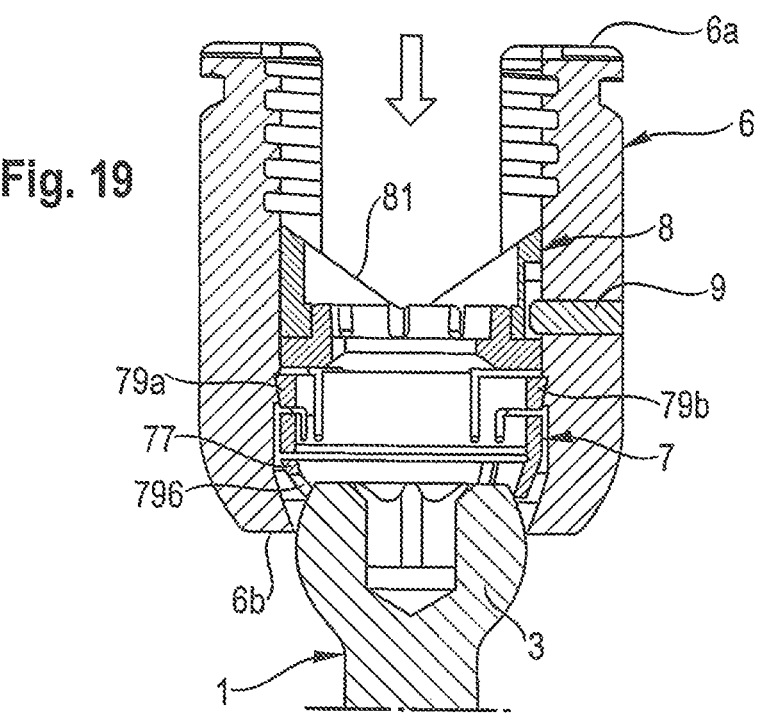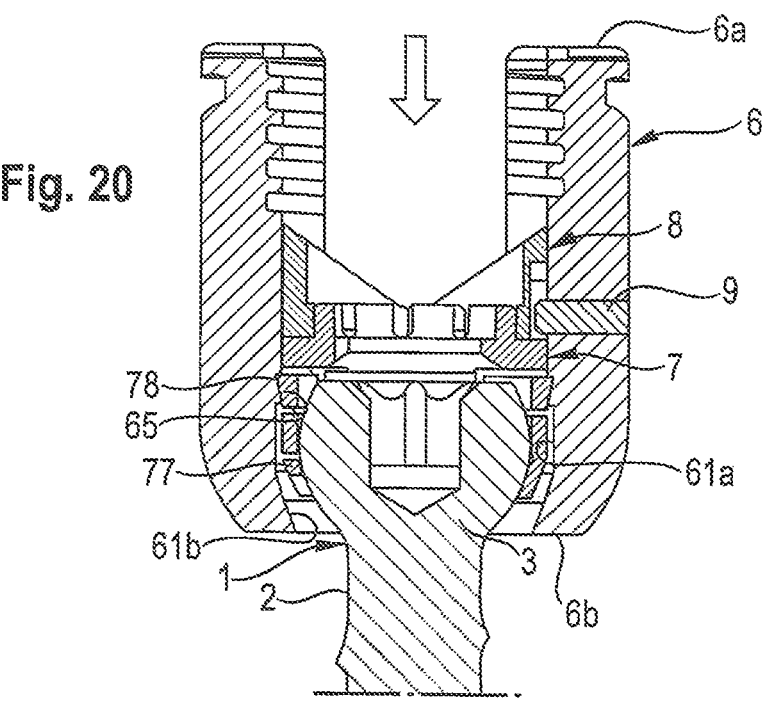

COUPLING ASSEMBLY FOR COUPLING A ROD TO A BONE ANCHORING ELEMENT, POLYAXIAL BONE ANCHORING DEVICE AND MODULAR STABILIZATION DEVICE

CROSS-REFERENCE TO RELATED APPLICATION(S)

This application is a continuation of U.S. patent application Ser. No. 15/918,762, filed Mar. 12, 2018, which is a continuation of U.S. patent application Ser. No. 14/490,569, filed Sep. 18, 2014, now U.S. Pat. No. 9,943,338, which claims priority to and the benefit of U.S. Provisional Patent Application Ser. No. 61/879,916, filed Sep. 19, 2013, the contents of which are hereby incorporated by reference in their entirety, and claims priority from European Patent Application EP 13 185 176.8, filed Sep. 19, 2013, the contents of which are hereby incorporated by reference in their entirety.

BACKGROUND

Field

The invention relates to a coupling assembly for coupling a rod to a bone anchoring element. The coupling assembly includes a receiving part with a recess for receiving the rod and an accommodation space for accommodating a head of the bone anchoring element, a pressure element to clamp the head, and a separate rod receiving element that is connectable to the pressure element and configured to support the rod. The pressure element has at least one spring portion that extends over a length in a circumferential direction and that is configured to engage a portion of an inner wall of the receiving part so that the pressure element can be held in a position that prevents an inserted bone anchoring element from being removed. The invention further relates to a bottom loading type polyaxial bone anchoring device with such a coupling assembly. Still further, the invention relates to a modular polyaxial bone anchoring device including the coupling assembly and at least two different rod receiving elements that can be used interchangeably with at least two associated closure mechanisms. The invention further relates to a modular stabilization device using the polyaxial bone anchoring device and at least two stabilizations rods having different diameters or one rod with at least two sections having different diameters.

DESCRIPTION OF RELATED ART

US 2010/0234902 A1 describes a receiving part for receiving a rod for coupling the rod to a bone anchoring element, the receiving part including a receiving part body with a channel for receiving the rod and defining an accommodation space for accommodating a head of a bone anchoring element and a pressure element at least partially provided in the accommodation space. In one embodiment the pressure element comprises two upstanding resilient fingers with outwardly directed portions at their free ends that can snap below pins extending through the wall of the receiving part in order to secure a pre-locking position of the pressure element in which the head can no longer be removed through the bottom end of the receiving part.

US 2010/0160980 A1 describes a locking mechanism and a method of fixation of a bone screw and a rod to the spine. The locking mechanism includes a body, an insert, a rod seat and a set screw. The body includes a bottom portion configured to receive the bone screw and the insert, but prevents the insert and the bone screw from passing therethrough once the insert and the bone screw are engaged. The rod seat is between the rod and the insert.

SUMMARY

It is an object of the invention to provide an improved coupling assembly for a bottom loading type polyaxial bone anchoring device, and such a polyaxial bone anchoring device, that allows for improved or easier handling during surgery. Furthermore, it is an object to provide a modular polyaxial bone anchoring device and a modular stabilization device that offers a greater variety of applications based on the modularity of the system.

The coupling assembly includes a pressure element that has at least one spring portion extending over a length in a circumferential direction and that is compressible in a radial direction. The spring portion is configured to engage an engagement structure at an inner wall of the receiving part. In a first engagement position, the spring portion engages a first engagement structure at the inner wall of the receiving part to prevent upward movement of the pressure element in the receiving part during insertion of the head of the bone anchoring element. In a second engagement position, the spring portion engages a second engagement structure at the inner wall of the receiving part in a pre-locking position, wherein the bone anchoring element is prevented from being pulled out from a lower opening of the receiving part.

In the pre-locking position of the pressure element, the head of the bone anchoring element may be held by a frictional force exerted by the pressure element onto the head. The frictional force may be such that pivoting of the head is still possible by applying a force that overcomes the frictional force.

According to an embodiment of the invention, the flexible portion of the pressure element has a circumferentially extending slit forming a slit ring or a portion of a slit ring at the bottom end of the pressure element. The slit ring can expand in a radial direction to allow for insertion of the head of the bone anchoring element. A force necessary for inserting the head into such a flexible portion of the pressure element is reduced compared to pressure elements that have, for example, a flexible portion with only longitudinal or coaxial slits. Therefore, easier assembly of the polyaxial bone anchoring device is facilitated.

The coupling assembly can be assembled in situ with a bone anchoring element that has already been inserted into a bone or a vertebra.

In an embodiment, the pressure element may have a recessed portion at its lower end that allows the shank of the bone anchoring element to pivot at a larger angle to one side compared to other sides of the pressure element. The pressure element further may have an indication feature configured to cooperate with an instrument to indicate the position of the recessed portion that provides the greater pivot angle. The enlarged pivot angle in one direction may be needed for special applications, for example, applications in the cervical spine.

A rod receiving element may have a groove with a shape that allows support of rods or rod sections having different diameters. Therefore, a modular stabilization device is provided that includes the bone anchoring device and a variety of rods with different diameter or one or more rods that have a change in diameter over the length of the rod. This renders the polyaxial bone anchoring device suitable for many different applications that depend on different diameters of the rods to be used.

In an embodiment, a first type of a rod receiving element has a first height in an axial direction that is smaller than the diameter of a rod to be supported. The first type of rod receiving element is configured to be used, for example, with a single part locking device that locks the head and the rod simultaneously.

In another embodiment, the rod receiving element has a second height in an axial direction that is greater than the largest diameter of a rod to be supported. The second type of rod receiving element is configured to be used, for example, with a two part locking device that locks the head and the rod independently.

A modular polyaxial bone anchoring device includes a bone anchoring element, the coupling assembly with the first type of rod receiving element and a single part locking device and the second type of rod receiving element with a two part locking device. The first type of rod receiving element with the single part locking device and the second rod receiving element with the two part locking device can be used interchangeably. The assembly of the polyaxial bone anchoring device is more easily facilitated. Therefore, a kit comprising the modular parts can be provided and part selection and assembly can be made on demand.

The modular polyaxial bone anchoring device furthermore can include several bone anchoring elements that may differ in regards to the length of the shank, the anchoring features of the shank, such as different thread types, thread pitches etc., different diameters of the shank, and in regards to cannulated on non-cannulated shanks.

The modularity in terms of the bone anchoring element and the type of closure element to be used, as well as the modularity in terms of the rods that can be employed, opens provides for a large variety of implants for the surgeon. In addition, the costs for stock-keeping may be reduced.

BRIEF DESCRIPTION OF THE DRAWINGS

Further features and advantages of the invention will become more apparent from the description of various embodiments using the accompanying drawings. In the drawings:

FIG. 3 shows a cross-sectional view of the bone anchoring device according to the first embodiment of FIGS. 1 and 2, the cross-section taken perpendicular to an axis of an inserted rod;

FIG. 4 shows a perspective view from above of a receiving part according to the first embodiment;

FIG. 5 shows a perspective view from the bottom of the receiving part shown in FIG. 4;

FIG. 6 shows a top view of the receiving part shown in FIGS. 4 and 5;

FIG. 7a shows a cross-sectional view of the receiving part shown in FIGS. 4 to 6 along line A-A in FIG. 6;

FIG. 7b shows an enlarged view of a detail of FIG. 7a;

FIG. 8 shows a perspective view from above of a pressure element according to a first embodiment;

FIG. 9 shows a perspective view from the bottom of the pressure element shown in FIG. 8;

FIG. 10 shows a side view of the pressure element shown in FIGS. 8 and 9;

FIG. 11 shows a top view of the pressure element shown in FIGS. 8 to 10;

FIG. 12 shows a cross-sectional view of the pressure element of FIGS. 8 to 11 along line B-B in FIG. 11;

FIG. 17 shows a cross-sectional view of a first step of assembling the coupling assembly according to the first embodiment;

FIG. 18a shows a cross-sectional view of a second step of assembling the coupling assembly according to the first embodiment;

FIG. 18b shows an enlarged cross-sectional view of a detail of FIG. 18a;

FIG. 19 shows a cross-sectional view of a first step of assembling the polyaxial bone anchoring device (e.g., with a bone anchoring element) according to the first embodiment;

FIG. 20 shows a cross-sectional view of a second step of assembling the polyaxial bone anchoring device according to the first embodiment;

FIG. 21b shows an enlarged view of a detail of FIG. 21a;

DETAILED DESCRIPTION

Figure 1:
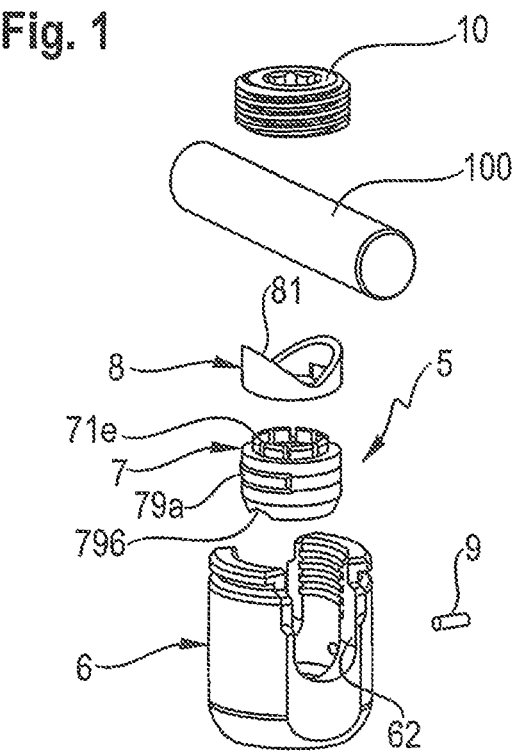
FIG. 1 shows a perspective exploded view of a first embodiment of a bone anchoring device.
Figure 2:
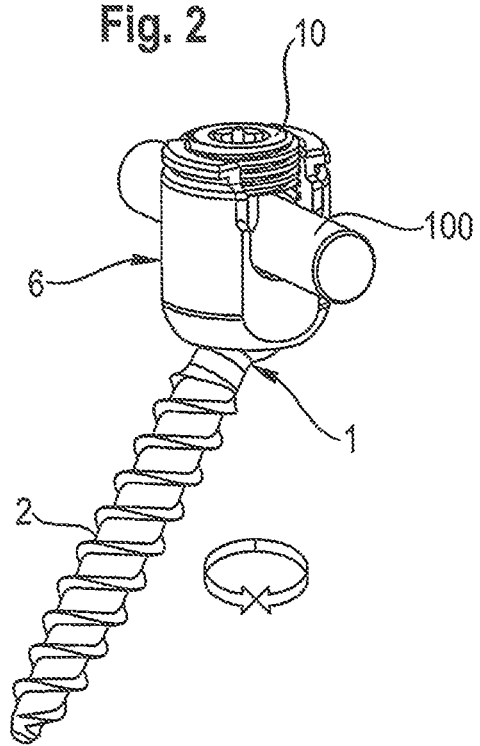
FIG. 2 shows a perspective view of the bone anchoring device of FIG. 1 in an assembled state.
Figure 13:
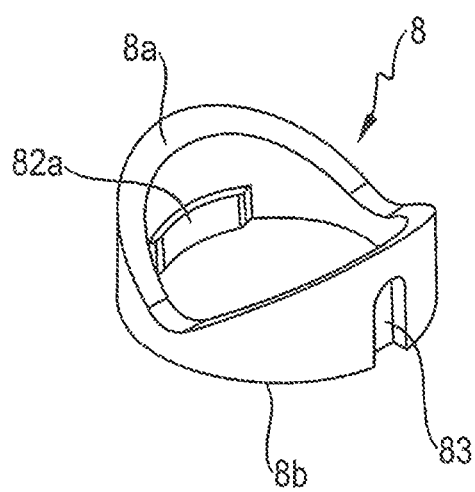
FIG. 13 shows a perspective view from above of a rod receiving element according to a first embodiment.
Figure 14:
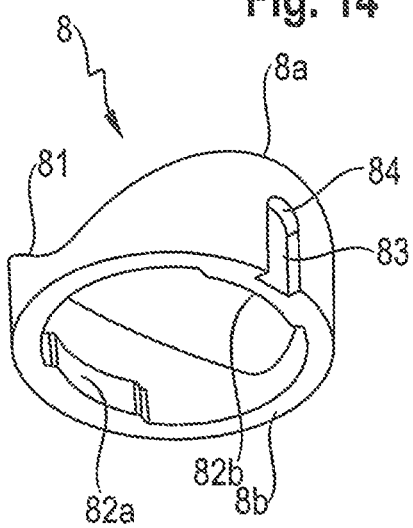
FIG. 14 shows a perspective view from the bottom of the rod receiving element of FIG. 13.
Figure 15:
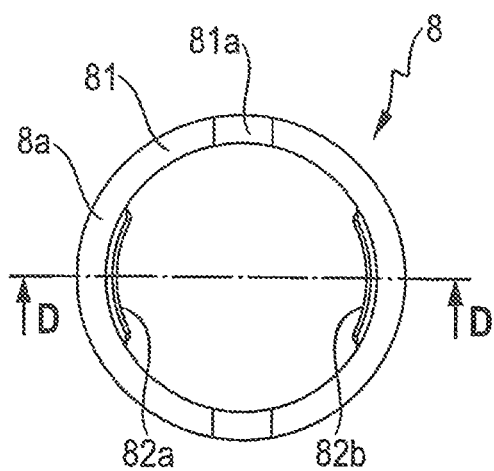
FIG. 15 shows a top view of the rod receiving element shown in FIGS. 13 and 14.
Figure 16:
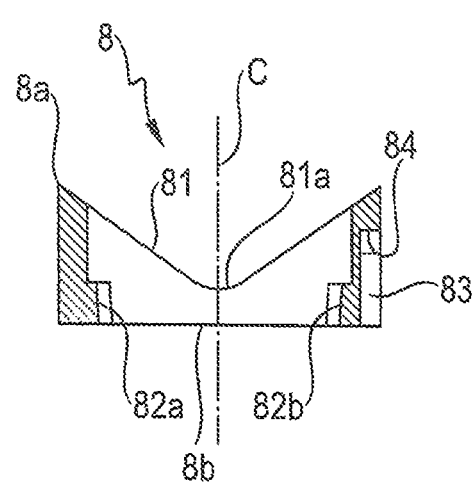
FIG. 16 shows a cross-sectional view of the rod receiving element of FIGS. 13 to 15 along line D-D in FIG. 15.

Referring to FIGS. 1 and 2, a bone anchoring device according to a first embodiment includes a bone anchoring element 1 in the form of a bone screw having a shank 2 that is at least partially provided with a bone thread, and a head 3. The head 3 has a spherical segment-shaped surface portion including a greatest outer diameter E of the sphere and a flat free end with a recess 4 for engagement with a screwing-in tool.

The bone anchoring device further includes a coupling assembly 5 for receiving a stabilization rod 100 and for coupling the stabilization rod 100 to the bone anchoring element 1. The coupling assembly 5 includes a receiving part 6 for receiving the head 3 of the bone anchoring element 1 and for receiving the rod 100, and a pressure element 7 configured to be arranged in the receiving part 6. The pressure element 7 is utilized for locking the head 3 in the receiving part 6. The coupling assembly further includes a rod receiving element 8 that is connectable to the pressure element 7 and that serves for providing support for an inserted rod 100. A pin 9 may be employed for securing a rotational position of the rod receiving element 8, so that a support surface for the rod 100 is aligned with a recess of the receiving part 6 through which the rod 100 extends as further described below.

Further, a locking element 10 in the form of an inner screw is provided for securing the rod 100 in the receiving part 6 and for exerting a force via the rod 100 onto the rod receiving element 8 and the pressure element 7 to lock the head 3 in the receiving part 6. The locking element 10 in this embodiment is a single part locking element that is configured to lock the head 3 of the bone anchoring element 1 and the rod 100 simultaneously.

The receiving part 6 will now be explained with reference to FIGS. 1 to 7b. The receiving part 6 has a first end 6a that is a top end and an opposite second end 6b that forms a bottom end, and a central axis of symmetry C passing through the first end 6a and the second end 6b. A bore 61 is provided that is coaxial with the central axis C. In a first region adjacent to the first end 6a the receiving part 6 has a substantially U-shaped recess 62 with a bottom directed towards the second end 6b and two free lateral legs 62a, 62b extending towards the first end 6a. On the legs 62a, 62b, and internal thread 63 is provided that cooperates with the locking element 10. The channel formed by the U-shaped recess 62 is sized so as to receive the rod 100 therein for connecting at least two bone anchoring devices. In the region of the legs 62a, 62b to substantially a height in an axial direction defined by the bottom of the U-shaped recess 62, the bore 61 has a first diameter. In a region below the legs 62a, 62b, the bore 61 has a widened portion 61a with a diameter greater than the first diameter of the bore 61. Between the second end 6b and the widened portion 61a, the bore 61 has a narrowing portion 61b that tapers and narrows towards the second end 6b with a cone angle. An opening 64 is provided at the second end 6b, the diameter of the opening 64 being larger than the largest diameter E of the head 3 to allow the insertion of the head 3 from the second end 6b of the receiving part 6. The widened portion 61a and the narrowing portion 61b define an accommodation space for the head 3 of the bone anchoring element 1.

Between the portion of the bore 61 with the first diameter that is located adjacent to the first end 6a and the widened portion 61a of the bore 61, there is a recess 65 that extends circumferentially at the inner wall of the receiving part 6 and that has a substantially conical shape widening in a direction from the second end 6b towards the first end 6a. As can be seen in detail in FIG. 7b, the size of the recess 65 is such that, at the end facing the second end 6b of the receiving part 6, the recess 65 has an inner diameter corresponding substantially to the first diameter of the portion of the bore 61 nearer to the first end 6a, and therefore forms an annular inwardly protruding edge 66 at the upper end of the widened portion 61a. The protruding edge 66 defines a first stop. An upper or opposite end or region of the recess 65 has a greater diameter than the portion of the bore 61 nearer to the first end 6a, and forms a second edge 67 that defines a second stop. A cone angle of the recess 65 is such that a spring portion provided at the pressure element 7 can be held in the recess 65 in a pre-stressed manner, as further described below.

At at least one of the legs 62a, 62b, a transverse bore 68 is provided that extends through the leg, for example through the leg 62b, in a direction substantially perpendicular to the central axis C for receiving the pin 9. The pin 9 has a length such that once the pin 9 is inserted into the transverse bore 68, the pin 9 extends a short distance into the bore 61 to provide a stop for securing a rotational position of the rod receiving element 8, as further described below. The pin 9 may be flush with an outer surface of the receiving part 6 when inserted.

Referring to FIGS. 8 to 12, the pressure element 7 has a first end 7a and a second end 7b. The second end 7b of the pressure element 7 is configured to be closer to the second end 6b of the receiving part 6 than the first end 7a of the pressure element 7 is to the second end 6b of the receiving part 6 when the pressure element 7 is arranged in the receiving part 6. The pressure element 7 is a substantially cap-like part that has a hollow interior chamber 71 with an opening 72 at the second end 7b, wherein the hollow interior chamber 71 is configured and sized to accommodate and hold the head 3 of the bone anchoring element 1 therein. An opening 73 near the first end 7a that communicates with the hollow interior chamber 71 allows access to the recess 4 of an inserted head 3 with a tool from the first end 7a of the pressure element 7. The lower opening 72 is sized to allow the insertion of the head 3 from the second end 7b. A lower portion 71a of the pressure element 7 adjacent to the second end 7b tapers or narrows towards the second end 7b with an outer surface, which in this embodiment matches or corresponds substantially to the shape of the narrowing portion 61b of the receiving part 6.

At a distance from the second end 7b, a circumferentially extending slit 74 is provided. The slit 74 extends around the central axis C of the pressure element 7 along a plane substantially perpendicular to the central axis C. Further, the slit 74 extends around more than 180°, and preferably more than 270°, and further preferably more than 340° around the central axis C. By means of the slit 74, a ring-shaped portion at the second end 7b is provided that is integrally connected to the rest of the pressure element 7 by a wall portion forming a connecting strip 75. The connecting strip 75 has a length in the circumferential direction such that it provides a stable connection of the ring-shaped portion to the rest of the pressure element 7. At one end of the circumferentially extending slit 74, there is a substantially vertical slit 76 that extends from the second end 7b fully through the ring-shaped portion into the circumferentially extending slit 74. By means of this, the ring-shaped portion is cut through or split in a circumferential direction and forms a slit ring 77 that can be expanded and compressed in a radial direction. The outer surface of the slit ring 77 forms the narrowing outer surface of the lower portion 71a that narrows towards the second end 76 of the pressure element 7. A position and size of the slit ring 77 is such that when the head 3 of the bone anchoring element 1 is inserted through the opening 72 into the hollow interior chamber 71, the slit ring 77 expands so that the width of the vertical slit 76 becomes larger, and when the head 3 has been fully inserted into the hollow interior chamber 71, the slit ring 77 encompasses the head 3 at or below a position of the largest diameter E of the head 3 in a direction towards the shank 2. An inner surface of the pressure element 7 in the region of the slit ring 77 may be spherical segment-shaped, with a size that is adapted or corresponds to the size of the head 3.

A portion 71b of the pressure element 7 adjacent to the slit ring 77 is substantially cylindrical with an outer diameter that is smaller than an inner diameter of the widened portion 61a of the receiving part 6. A corresponding inner surface of the portion 71b is substantially cylindrical with an inner diameter corresponding to or slightly larger than the largest outer diameter E of the head 3.

The pressure element 7 further has an intermediate portion 71c that continues from or is connected to the cylindrical portion 71b. The intermediate portion 71c has a conical outer surface that widens towards the first end 7a of the pressure element 7. An outermost edge 78 of the intermediate portion 71c that faces the first end 7a protrudes outward from the rest of the pressure element 7. The cone angle of the intermediate portion 71c corresponds substantially to the cone angle of the conical recess 65 of the receiving part 6. An inner surface of the intermediate portion 71c is cylindrical and has an inner diameter corresponding to the inner diameter of the cylindrical portion 71b.

Next, an upper cylindrical portion 71d extends from the intermediate portion 71c towards the first end 7a of the pressure element 7. The upper cylindrical portion 71d has an outer diameter that may be substantially the same as the outer diameter of the lower cylindrical portion 71b and that is in particular slightly smaller than the inner diameter of the bore 61. The upper cylindrical portion 71d defines the coaxial bore 73 and a spherical segment-shaped section 710 that may make up part of the hollow interior chamber 71 and has a radius adapted to the spherical segment-shaped head 3 of the bone anchoring element 1. Hence, when the head 3 of the bone anchoring element 1 is inserted into the hollow interior chamber 71 and tilted, as can be seen, for example, in FIG. 3, the spherical segment-shaped section 710 contacts the surface of the head 3.

In the intermediate portion 71c, two spring portions 79a, 79b are provided. The spring portions 79a, 79b are ring segment-shaped and extend around the central axis C around an angle α of approximately 90°, as can be seen in particular in FIG. 11. However, the ring segment-shaped spring portions 79a, 79b can extend around a smaller or a larger angle around the central axis C, depending on the desired flexibility to be achieved.

The spring portions 79a, 79b are formed by slits that extend substantially coaxially to the central axis C and slits that extend substantially in a circumferential direction around the pressure element 7. Referring in particular to FIG. 10, the spring portion 79a is formed by the following slits. A first vertical slit 791a extends from the lower cylindrical portion 71b of the pressure element 7 through the intermediate portion 71c and to approximately the upper cylindrical portion 71d in a substantially vertical or coaxial direction with respect to the central axis C. A second vertical slit 792a is spaced apart from the first vertical slit 791a in a circumferential direction and extends from the lower cylindrical portion 71b of the pressure element 7 to the intermediate portion 71c. A first or upper horizontal slit 793a extends from the first vertical slit 791a in a circumferential direction a distance around the pressure element 7 that defines the angle α of the spring portion around the central axis C. A second or lower horizontal slit 794a extends from the upper end of the second vertical slit 792a in a circumferential direction a distance around the pressure element 7 that is slightly less than the angle α around the central axis C. A third vertical slit 795a connects the ends of the first horizontal slit 793a and the second horizontal slit 794a on a side opposite the first and second vertical slits 791a, 792a. Widths of the vertical slits 791a, 792a, 795a in a circumferential direction may be greater than widths of the horizontal slits 793a, 794a in an axial direction. Further, the width of the upper horizontal slit 793a may be the same as the width of the lower horizontal slit 794a.

By the first and second vertical slits 791a, 792a, a strip is formed that connects the ring segment-shaped spring portion 79a with the rest of the pressure element 7. By the third vertical slit 795a, the ring segment-shaped spring portion 79a is provided with a free end in the circumferential direction.

The second ring segment-shaped spring portion 79b is formed identically to the first spring portion 79a and has a first vertical slit 791b, a second vertical slit 792b, and a third vertical slit 795b, as well as a first upper horizontal slit 793b and a second lower horizontal slit 794b. The ring segment-shaped spring portions 79a, 79b are arranged mirror-symmetrical with respect to a mirror plane that contains the central axis C and extends between the first vertical slit 791a, 791b of each spring portion, as depicted in particular in FIG. 12. Hence, the free ends of the ring segment-shaped spring portions 79a, 79b point towards each other in the circumferential direction.

The spring portions 79a, 79b are compressible and expandable in a radial direction. When the pressure element 7 is inserted into the bore 61 of the receiving part 6, the spring portions 79a, 79b are slightly compressed so that the pressure element 7 can move downward in the bore 61 (i.e., towards the second end 6b). Once the spring portions 79a, 79b have passed the portion of the bore 61 having the first diameter, they are configured to resiliently snap into the conical recess 65.

The pressure element 7 further includes adjacent to the first end 7a, a plurality of upstanding ring segment-shaped projections 71e that are spaced apart in a circumferential direction and that are slightly resilient. An outer surface of the projections 71e may be slightly tapered so as to provide for a safe connection with the rod receiving element 8, as further described below. An inner surface of the projections 71e may be cylindrical. The upstanding projections 71e are spaced apart from or recessed from an outer surface of the upper cylindrical portion 71d, and surround the coaxial bore 73.

Adjacent to the second end 7b, there is a recessed portion 796 at the lower edge of the pressure element 7 that is formed by the lower edge of the slit ring 77. The recessed portion 796 has a shape and size such that the shank 2 of the bone anchoring element 1 can abut at a larger pivot angle against the lower edge of the pressure element 7 when bone anchoring element 1 pivots in the direction of the recessed portion 796, as compared to other directions. Therefore, the recessed portion 796 provides for an enlarged pivot angle in one direction. As can be seen in FIG. 10, the recessed portion 796 may be aligned approximately at a middle of one of the spring portions 79a, 79b. A second recessed portion 797 is provided at a corresponding circumferential position in the inner wall of the upper cylindrical portion 71d. The second recessed portion 797 serves for indicating the position of the first recessed portion 796, for example, when the pressure element 7 is engaged with a tool (not shown) that includes an engagement portion to engage the second recessed portion 797. Such a tool could have a visual indication on its handle, for example, that shows the user the position of the second recessed portion 797, and as a consequence thereof, the position of the first recessed portion 796. Hence, the position of the first recessed portion 796 that provides for the enlarged pivot angle can be identified even if the polyaxial bone anchoring device has already been implanted into a bone or a vertebra. The tool can also be used to engage the second recessed portion 797 in a form fit manner, and to rotate the pressure element 7 to adjust the orientation or direction of the first recessed portion 796.

With reference to FIGS. 3 and 13 to 16, the rod receiving element 8 will be described. The rod receiving element 8 is a substantially hollow cylindrical part having a first end 8a and an opposite second end 8b. A groove 81 having a substantially V-shaped cross section with a rounded bottom 81a extends from the first end 8a in the direction of the second end 8b, as can be seen in particular in FIGS. 13 and 16. The groove 81 defines a longitudinal direction that is parallel to the longitudinal axis of the rod 100 when the rod 100 is inserted. The groove 81 provides a support surface for supporting the rod 100. Referring to FIG. 3, the rod 100 has a circular cross section and is supported in the groove 81 along two contact lines P1, P2, that extend in a direction parallel to the rod axis. Depending on the diameter of the rod section that is supported by the groove 81, the contact lines P1, P2 are located more towards the bottom 81a of the groove 81 for a rod with a smaller diameter, or more towards the first end 8a of the groove 81 for a rod with a larger diameter, when compared to the rod 100 depicted in FIG. 3. Hence, the groove 81 is configured to support different rods having different diameters or different rod sections of a single rod that have different diameters.

Adjacent to the second end 8b, two opposite annular segment-shaped protrusions 82a, 82b are provided that extend towards the central axis C in a radial direction and along a certain length in the circumferential direction. A height of the annular segment-shaped protrusions 82a, 82b in the axial direction measured from the second end 8b corresponds to a height of the upstanding projections 71e of the pressure element 7. Furthermore, an inner surface of the annular segment-shaped protrusions 82a, 82b is slightly tapered and extends closer to the central axis C towards the second end 8b, and is configured to cooperate with the tapered outer surface of the upstanding projections 71e of the pressure element 7. Once the annular segment-shaped protrusions 82a, 82b engage the outer wall of the upstanding projections 71e of the pressure element 7, the upstanding projections 71e are slightly compressed and abut against the annular segment-shaped protrusions 82a, 82b so that the pressure element 7 is connected to the rod receiving element 8 and held by a frictional force. The location of the center of the annular segment-shaped protrusions 82a, 82b in a circumferential direction is at substantially 90° with respect to the bottoms 81a of the groove 81.

In the outer wall of the rod receiving element 8 on one side of the groove 81, an elongate recess 83 that extends substantially parallel to the central axis C is provided. The elongate recess 83 has a closed end 84 towards the first end 8a that serves as an abutment for the pin 9. By the elongate recess 83, a securing element is provided that also secures a correct or desired rotational position of the rod receiving element 8. The elongate recess 83 is open towards the second end 8b.

In the described embodiment, depth of the groove 81 is smaller than a largest diameter of a rod that can be supported by the rod receiving element 8. In other words, the first end 8a will be located below a top surface of a rod with a largest diameter that can be supported by the rod receiving element 8.

An outer diameter of the rod receiving element 8 is only slightly smaller than an inner diameter of the bore 61 of the receiving part and is preferably flush with an outer diameter of the upper cylindrical portion 71d of the pressure element 7 when the pressure element 7 and the rod receiving element 8 are assembled together as shown in FIG. 3.

The bone anchoring device, as a whole or partially, is made of a bio-compatible material, such as a bio-compatible metal or a metal alloy, for example titanium, stainless steel, of a nickel titanium alloy, for example, nitinol, or of bio-compatible plastic materials, such as, for example, polyetheretherketone (PEEK).

Referring to FIG. 17, the coupling assembly 5 is assembled by pre-assembling the pressure element 7 and the rod receiving element 8, such that the upstanding projections 71e are inserted and held between the annular segment-shaped protrusions 82a, 82b of the rod receiving element 8. The orientation of the pressure element 7 relative to the groove 81 of the rod receiving element 8 is such that the center of the spring portions 79a, 79b may initially be located in a circumferential direction at an angle of substantially 90° measured from the longitudinal axis of the groove 81. The pre-assembled pressure element 7 with the rod receiving element 8 is inserted from the first end 6a of the receiving part, with the second end 7b of the pressure element 7 facing in the direction of the second end 6b of the receiving part 6. During insertion, the spring portions 79a, 79b are compressed in a radial direction because the inner diameter of the portion of the bore 61 with the first diameter in the receiving part 6 has a smaller diameter than the outermost edge 78 of the spring portions 79a, 79b.

Referring to FIGS. 18a and 18b, as soon as the pressure element 7 is in a position in which the outermost edge 78 of the spring portions 79a, 79b has reached the conical recess 65 in the receiving part 6, the spring portions 79a, 79b snap behind the protrusion 67 that forms the upper edge of the conical recess 65. Thereby, the spring portions 79a, 79b are configured to radially expand into the conical recess 65. Thereafter, the pin 9 is inserted into the transverse bore 68 until a front face of the pin 9 extends into the elongate recess 83 provided at the rod receiving element 8. The pin 9 serves for securing the pressure element 7 and the rod receiving element 8 against inadvertent rotation, so that the U-shaped recess 62 of the receiving part and the groove 81 of the rod receiving element 8 remain aligned. In this condition, the coupling assembly 5 is pre-assembled and can be used for coupling to a bone anchoring element 1 and to a rod 100. In the pre-assembled condition, it is still possible to rotate the pressure element 7 with respect to the rod receiving element 8, and therefore also with respect to the receiving part 6, so that the orientation of the first recessed portion 796 that defines the direction having the enlarged pivot angle can be adjusted.

Referring further to FIGS. 19 and 20, the use of the coupling assembly 5 together with a bone anchoring element 1 will be explained. As depicted in FIG. 19, first, a suitable bone anchoring element 1 is selected. The bone anchoring element 1 may be connected to the coupling assembly 5 first, and thereafter inserted into a bone part or a vertebra. Alternatively, the bone anchoring element 1 can be placed first into the implantation site in a patient's body without the coupling assembly 5 being connected thereto. As shown in FIG. 19, the head 3 enters the receiving part 6 through the lower opening 64 and enters the hollow interior chamber 71 of the pressure element 7 through the open second end 7b of the pressure element 7. When the head touches the slit ring 77 of the pressure element 7, the pressure element 7 can not move upward towards the first end 6a of the receiving part 6 because the upper surfaces of the spring portions 79a, 79b abut against the upper edge 67 of the conical recess 65 that forms the second stop.

As shown in FIG. 20, further insertion of the head 3 upwards into the hollow interior chamber 71 expands the slit ring 77 within the widened portion 61a of the bore 61 of the receiving part 6. The head 3 can then be completely inserted into the pressure element 7. Because the slit ring 77 does note expand at the connection strip 75 the insertion of the head 3 may not be precisely coaxial with the central axis C, but instead may be slightly out of or misaligned with the central axis C. By the further insertion of the head 3, the slit ring 77 may be expanded to a maximum extent to allow the head 3 to enter the upper portion of the hollow interior chamber 71 until the head 3 rests in the spherical segment-shaped portion of the chamber 71 that is adjacent to the second end 7b. Here, the slit ring 77 can elastically contract around the head 3 as shown in FIG. 20.

Figure 21A:
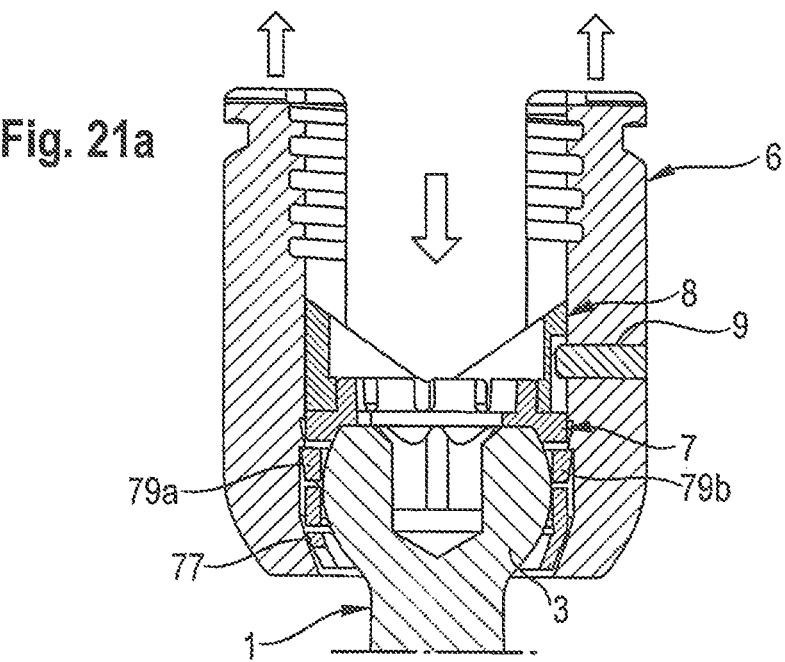
FIG. 21a shows a cross-sectional view of a third step of assembling the polyaxial bone anchoring device according to the first embodiment.
Figure 21B:
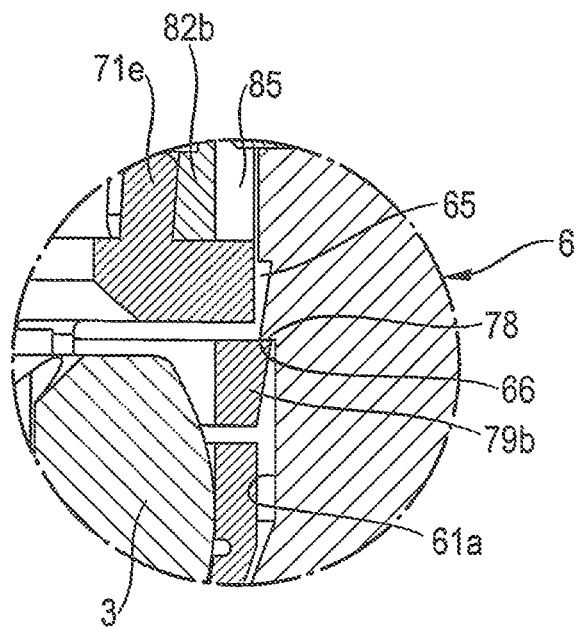

Referring to FIGS. 21a and 21b, pulling the receiving part 6 upwards as illustrated, and/or pressing down the pressure element 7 with an instrument (not shown) presses the slit ring 77 into the narrowing portion 61b of the receiving part 6. The conical shape of the recess 65 at the inner wall of the receiving part 6 provides an inclined surface that allows the spring portions 79a, 79b to slide along the inner wall when the pressure element 7 is further moved downwards towards second end 6b, thereby gradually compressing the spring portions 79a, 79b again until the upper outer edges 78 of the spring portions 79a, 79b snap behind the second inner protrusions 66 in the receiving part 6. In this position, the pressure element 7 is again prevented from moving upwards towards the first end 6a of the receiving part 6 by the first stop provided by the inner protruding edge 66. The head 3 is already clamped by the slit ring 77. Because the slit ring 77 is located between the head 3 and the narrowing portion 61b of the receiving part 6, the slit ring 77 is prevented from expanding, and so the head 3 is prevented from falling out or being pushed out through the lower opening 64. This is the pre-locking condition or position.

In clinical use, usually at least two bone anchoring devices are inserted into the bone and the respective receiving parts 6 are aligned. The heads 3 of the bone anchoring elements 1 are held in the respective pressure elements 7 by a frictional force. Hence, the receiving parts 6 can be easily aligned manually, and their angular positions are maintained by the frictional force between the heads 3 and the pressure elements 7.

Finally, referring to FIG. 3, the rod 100 is inserted into the receiving part 6. The rod 100 rests on the upper surface of the groove 81 at substantially two longitudinal contact areas P1, P2. Then, the locking element 10 is screwed between the legs 62a, 62b of the receiving part 6. Tightening of the locking element 10 advances the locking element 10 towards the rod 100 until it contacts an upper surface of the rod 100. The downward force applied by the locking element 10 is transferred from the rod 100 to the pressure element 7. Finally, the head 3 and the rod 100 are locked relative to the coupling assembly 5. The head 3 can be locked in a specific angular position with respect to the receiving part 6.

The bone anchoring element 1 can be pivoted in the direction of the recessed portion 796 at the second end 7b of the pressure element 7 to a greater angle relative to the receiving part 6 than in an opposite or other directions.

Figure 22:
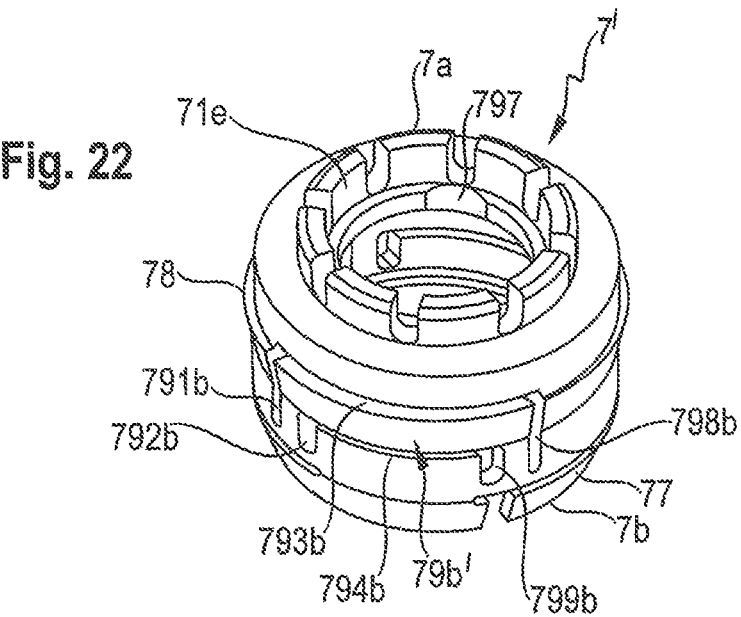
FIG. 22 shows a perspective view of a pressure element of a coupling assembly according to a second embodiment.
Figure 23:
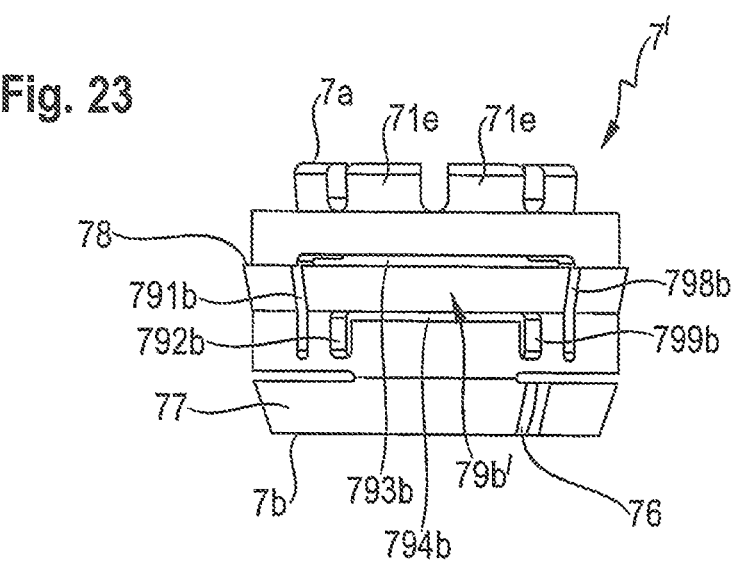
FIG. 23 shows a side view of the pressure element shown in FIG. 22.
Figure 24:
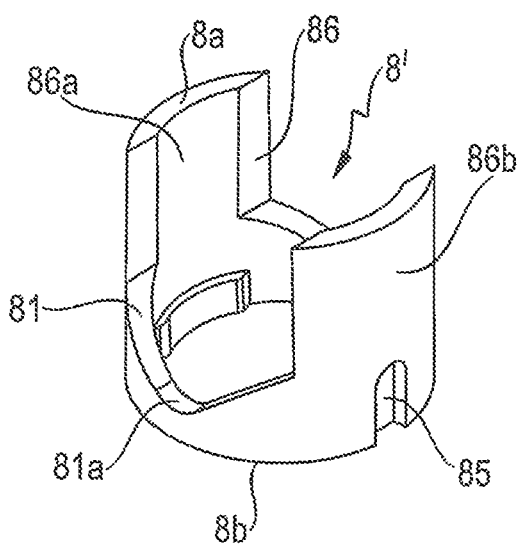
FIG. 24 shows a perspective view from above of a rod receiving element of a coupling assembly according to a second embodiment.
Figure 25:
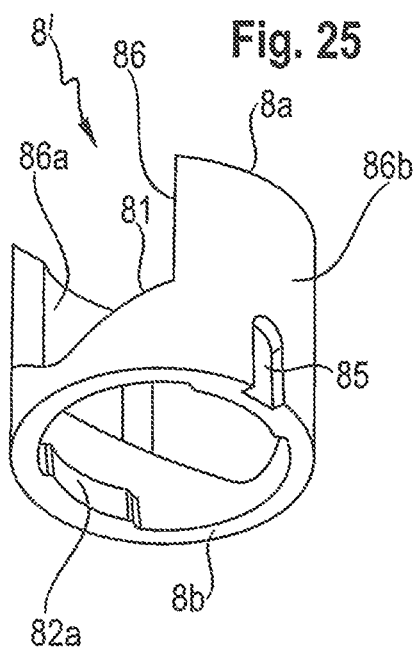
FIG. 25 shows a perspective view from the bottom of the rod receiving element shown in FIG. 24.
Figure 26:
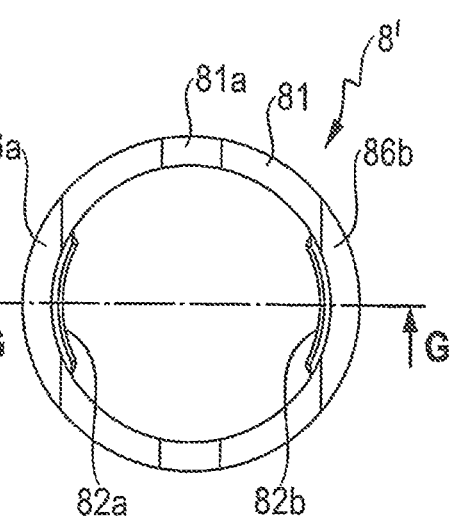
FIG. 26 shows a top view of the rod receiving element shown in FIGS. 24 and 25.
Figure 27:
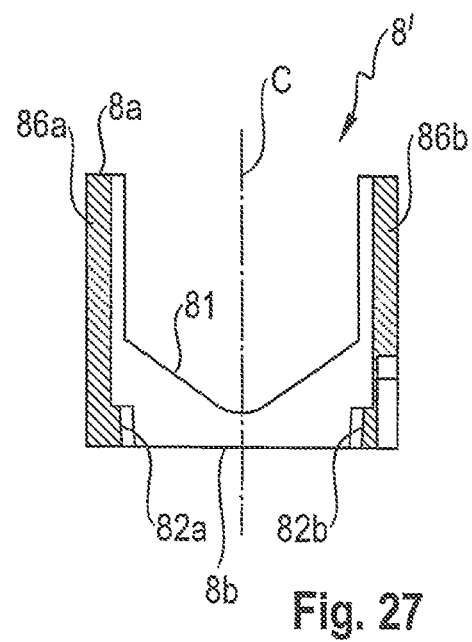
FIG. 27 shows a cross-sectional view of the rod receiving element shown in FIGS. 24 to 26 along line G-G in FIG. 26.

Referring to FIGS. 22 and 23, a second embodiment of the pressure element will be described. The pressure element 7' differs only in that the spring portions 79a', 79b' do not have a free end. Instead, each spring portion 79a', 79b', is attached at the respective ends of the ring segment-shaped portions via corresponding axially extending strips that are formed by two vertical slits 798a, 799a,798b, 799b, respectively, wherein slits 798a, 798b extend to the first horizontal slit 793a, 793b, and slits 799a, 799b extend to the second horizontal slit 794a, 794b, respectively.

A second embodiment of the rod receiving element will be described with reference to FIGS. 24 to 27. Parts and portions that are identical or similar to those of the first embodiment have the same reference numerals, and the descriptions thereof will not be repeated. The rod receiving element 8' includes two opposite upstanding legs 86a, 86b that extend upward from the rod supporting groove 81. The upstanding legs 86a, 86b are provided by a substantially rectangular recess 86 that is cut into the hollow cylindrical rod receiving element 8' starting from the first end 8a towards the second end 8b. The upstanding legs 86a, 86b have a height such that they extend above a top surface of an inserted rod 100 that rests in the rod supporting groove 81. This renders the rod receiving element 8' suitable for use with a two-part locking device 10' as depicted in FIG. 28.

The two-part locking device 10' includes an outer locking element 10a and an inner locking element 10b. The outer locking element 10a cooperates with the internal thread 63 of the receiving part 6 and is configured to abut against the first end 8a of the rod receiving element 8' according to the second embodiment. The inner locking element 10b can be screwed into a threaded hole of the outer locking element 10a and is configured to cooperate with the rod but not with the inserted rod receiving element 8'. When the two-part locking element 10' is used, the head 3 of the bone anchoring element 1 can be locked by exerting pressure with the outer locking element 10a only onto the rod receiving element 8' according to the second embodiment, and via the pressure element 7, 7' onto the head 3, while the rod can be locked independently by exerting pressure with the inner locking element 10b onto its surface, independently from the locking of the head 3.

Figure 28:
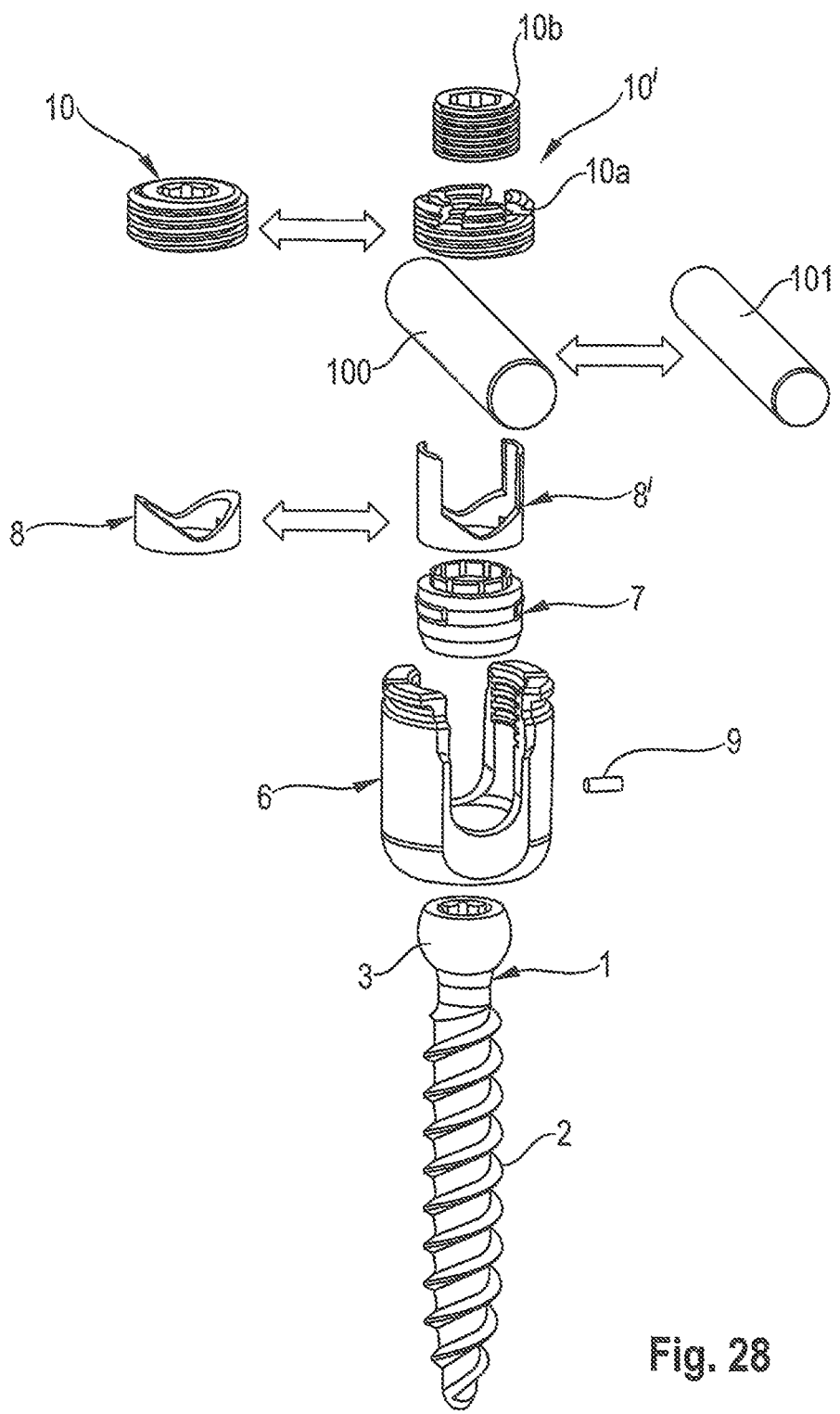
FIG. 28 shows a perspective schematic view of a modular polyaxial bone anchoring device.

FIG. 28 depicts a modular device for stabilizing bones or vertebrae, and includes a modular polyaxial bone anchoring device and different kinds of stabilization rods 100, 100' that have different rod diameters. The modular polyaxial bone anchoring device includes the receiving part 6 and an assembly kit including the rod receiving element 8 according to the first embodiment and the rod receiving element 8' according to the second embodiment that can be used interchangeably together with the pressure element 7, 7'. Corresponding to the first type of coupling assembly utilizing the rod receiving element 8, the single part locking device 10 can be used as part of the modular device, and corresponding to the second type of coupling assembly utilizing the rod receiving element 8', the two-part locking device 10' can be used as part of the modular device. In other embodiments, various other types of locking devices that are configured to cooperate with either the rod receiving element 8 or the rod receiving element 8' may also be employed.

A modular polyaxial bone anchoring device further includes at least one bone anchoring element 1, preferably a plurality of bone anchoring elements that may differ with respect to the lengths of the shanks, anchoring features of the shanks, such as different thread types, thread pitches, different diameters of the shanks, cannulated or non-cannulated shanks, or with respect to various other features. Because the polyaxial bone anchoring device is a bottom loading type polyaxial bone anchoring device, the assembly of the polyaxial bone anchoring device is easily made, for example, by the surgeon or any personnel assisting the surgeon, so that a suitable bone anchoring device can be provided on demand during or before surgery.

The modular stabilization device may further include at least two rods 100, 101 having different diameters and/or at least one rod having sections with different diameters.

Figure 29A:
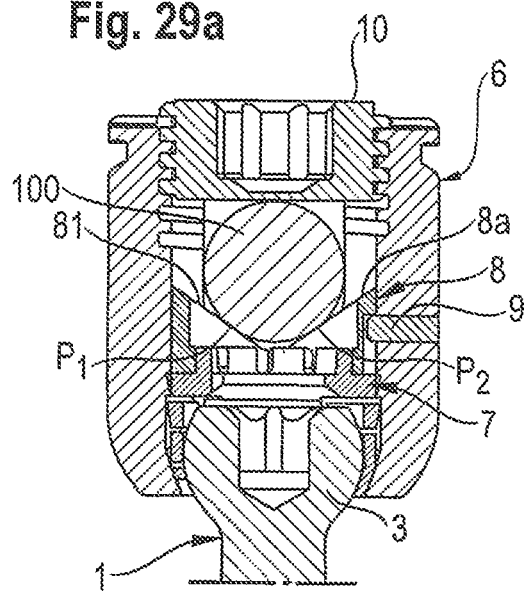
FIG. 29a shows a cross-sectional view of the polyaxial bone anchoring device according to the first embodiment with an inserted rod having a first diameter and a single part locking device.
Figure 29B:
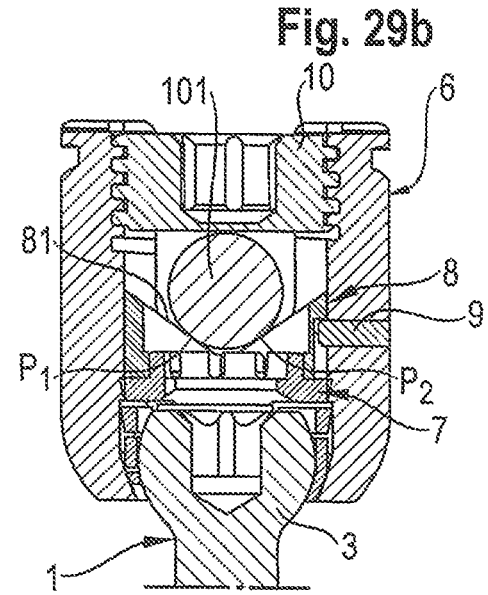
FIG. 29b shows a cross-sectional view of the polyaxial bone anchoring device according to the first embodiment with an inserted rod having a second diameter and a single part locking device.

FIGS. 29a to 30b show various combinations of the elements of the modular system depicted in FIG. 28. In FIG. 29a, the first type of coupling assembly using the first type of rod receiving element 8 is used together with a rod 100 of a larger diameter and a single part locking device 10. The locking device 10 exerts pressure onto the rod 100 and locks the rod and the head 3 simultaneously. In FIG. 29b, the first type of coupling assembly as shown in FIG. 29a is used together with a rod 101 having a smaller diameter than the rod 100 shown in FIG. 29a. The single part locking device 10 exerts pressure onto the rod 101 with a smaller diameter and simultaneously locks the head 3 and the rod 101. The rod 101 with the smaller diameter is safely clamped in the same manner as the rod 100 with the larger diameter.

Figure 30A:
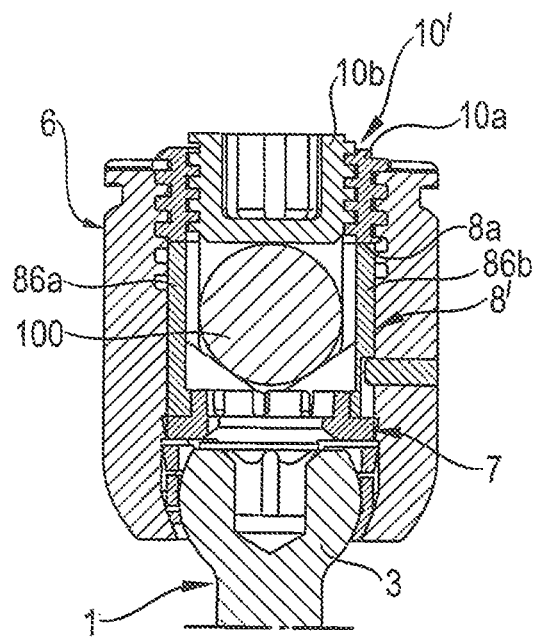
FIG. 30a shows a cross-sectional view of a polyaxial bone anchoring device according to the second embodiment with an inserted rod having a first diameter and a two part locking device.
Figure 30B:
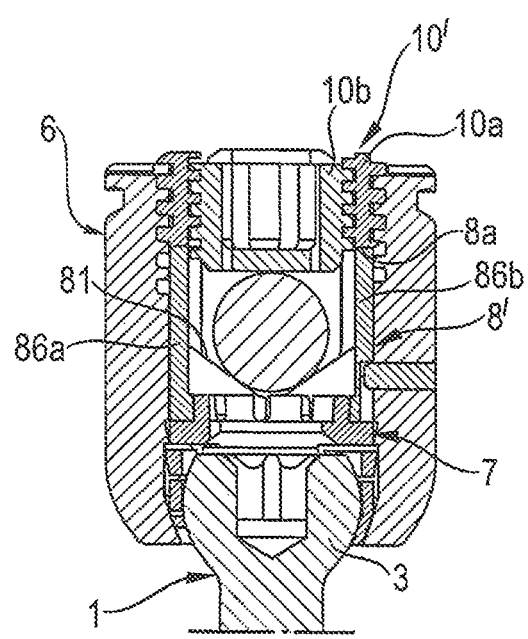
FIG. 30b shows a cross-sectional view of the polyaxial bone anchoring device according to the second embodiment with an inserted rod having a second diameter and a two part locking device.

In FIG. 30a, the second type of coupling assembly using the second type or rod receiving element 8' is used together with the rod 100 having a larger diameter and with a two-part locking device 10'. The outer locking element 10a acts on the first end 8a of the rod receiving element 8', which in turn transfers the force onto the pressure element 7 and locks the head 3. The rod 100 can still be moved in an axial direction, and can be locked independently by the inner locking element 10b that exerts pressure onto the rod 100 but not onto the head 3. FIG. 30b shows the same situation as in FIG. 30a, with the only difference being that the rod 101 having a smaller diameter than the rod 100 shown in FIG. 30a is used. The inner locking element 10b has to be screwed deeper into the outer locking element 10a in order to clamp the rod 101.

Various other modifications of the embodiments described above may also be contemplated. For example, the receiving part is not limited to the exact shape as shown. The recess 62 of the receiving part does not have to have an exact U-shape. The bore 61 can also have several sections with different widths, as long as the enlarged portion 61a that provides space for the expansion of the pressure element is provided. The narrowing portion at the bottom of the receiving part is shown to be tapered, but can also be rounded, for example. Also, the external surface of the lower portion at the bottom end of the pressure elements 7, 7' can be rounded. Combinations of the surfaces of the receiving part and the pressure element that cooperate to clamp the head can, for example, be tapered and tapered, tapered and rounded, rounded and tapered, or rounded and rounded, among other configurations.

The embodiments have been described with one single ring segment-shaped section on the pressure element that clamps the head. However, there may be more than one ring segment-shaped section to clamp the head in other embodiments.

Meanwhile, the horizontal and vertical slits in the pressure element need not to be exactly horizontal or exactly vertical, and instead, they may have inclinations or shapes that differ from a straight or a circular shape, in order to achieve different elastic properties.

In other embodiments, the interior hollow chamber of the pressure element and/or the head of the bone anchoring element can have different shapes that restrict the pivoting of the bone anchoring element relative to the receiving part or the pressure element to one single plane, so that the pivot connection is not polyaxial, but is instead monoplanar.

It is also possible to provide more than one, for example two or three, recessed portions at the second end of the pressure element, for having more than one direction that allows for an enlarged pivot angle. The recessed portion at the second end of the pressure element can also be omitted, so that the pivot angle is the same in all directions.

In addition, all kinds of rods can be used. While rods with a smooth surface are shown, roughened rods or rods having other structures may also be used. The rods may also be rods made of a flexible material, or may have flexibility through other means.

While a number of different embodiments are disclosed herein, it is appreciated that different components from the different embodiments can be mixed and matched to produce a variety of still other different embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling assembly for coupling a rod to a bone anchoring element, the coupling assembly comprising:
   a receiving part having a first end, a second end below the first end, and a central axis extending through the first and second ends, a recess at the first end for receiving the rod, and an accommodation space for accommodating a head of the bone anchoring element, the accommodation space having an opening at the second end for inserting the head; and
   a pressure element positionable at least partially in the accommodation space to exert pressure on the head, wherein the pressure element comprises at least one spring portion which extends circumferentially around the central axis from a first end that is connected axially to another portion of the pressure element to a free second end that is spaced apart axially from and resiliently movable relative to other portions of the pressure element, wherein at least the second end of the spring portion is configured to engage a downwardly facing engagement surface at an inner wall of the receiving part to restrict axial movement of the pressure element towards the first end of the receiving part.

2. The coupling assembly of claim 1, wherein the engagement surface is formed by an inward protrusion that is configured to engage the spring portion.

3. The coupling assembly of claim 1, wherein the engagement surface is at a side of the accommodation space that is positioned closer to the first end of the receiving part.

4. The coupling assembly of claim 1, wherein an end of the pressure element has a recessed portion that allows pivoting of the bone anchoring element to a greater angle relative to the receiving part in a radial direction of the recessed portion compared to other radial directions.

5. A polyaxial bone anchoring device comprising the coupling assembly of claim 1 and the bone anchoring element having a shank for anchoring to a bone and the head.

6. The polyaxial bone anchoring device of claim 5, wherein when the second end of the spring portion engages the engagement surface of the receiving part, the pressure element exerts a frictional force on the head that temporarily holds an angular position of the shank relative to the receiving part.

7. The coupling assembly of claim 1, wherein the pressure element defines a hollow interior chamber for holding and clamping the head of the bone anchoring element therein.

8. The coupling assembly of claim 1, further comprising a rod receiving element that is separable from the pressure element and that comprises a body with an upwardly facing surface that defines a groove for supporting the rod.

9. The coupling assembly of claim 1, wherein the spring portion is radially compressible.

10. The coupling assembly of claim 1, wherein the second end of the spring portion is closer to the first end of the receiving part than the first end of the spring portion is to the first end of the receiving part.

11. The coupling assembly of claim 1, wherein the spring portion is a first spring portion, and wherein the pressure element further comprises a second spring portion which extends circumferentially in a direction opposite the first direction around the central axis from a first end that is connected to yet another portion of the pressure element to a free second end.

12. A coupling assembly for coupling a rod to a bone anchoring element, the coupling assembly comprising:
   a receiving part having a first end, a second end below the first end, and a central axis extending through the first and second ends, a recess at the first end for receiving the rod, and an accommodation space for accommodating a head of the bone anchoring element, the accommodation space having an opening at the second end for inserting the head; and
   a pressure element positionable at least partially in the accommodation space to exert pressure on the head, wherein the pressure element comprises at least a first spring portion which extends circumferentially in a first direction around the central axis and axially towards the first end of the receiving part from a first end that is connected axially to a first region of the pressure element to a free second end that is spaced apart axially from other portions of the pressure element, and a second spring portion which extends circumferentially in a direction opposite the first direction around the central axis and axially towards the first end of the receiving part from a first end that is connected axially to a second region of the pressure element to a free second end that is spaced apart axially from other portions of the pressure element.

13. The coupling assembly of claim 12, wherein the pressure element defines a hollow interior chamber for holding and clamping the head of the bone anchoring element therein.

14. The coupling assembly of claim 12, wherein the first and second spring portions are radially compressible.

15. The coupling assembly of claim 12, wherein the first and second regions of the pressure element at which the first and second spring portions are respectively connected are spaced apart circumferentially from one another.

16. The coupling assembly of claim 12, wherein the first and second spring portions each extends circumferentially approximately 90° around the pressure element.

17. A coupling assembly for coupling a rod to a bone anchoring element, the coupling assembly comprising:
   a receiving part having a first end, a second end below the first end, and a central axis extending through the first and second ends, a recess at the first end for receiving the rod, and an accommodation space for accommodating a head of the bone anchoring element, the accommodation space having an opening at the second end for inserting the head; and
   a pressure element positionable at least partially in the accommodation space to exert pressure on the head, wherein the pressure element comprises at least one spring portion which extends circumferentially around the central axis from a first end that is connected axially to another portion of the pressure element to a free second end that is spaced apart axially from other portions of the pressure element,
   wherein a ring-shaped portion that is positioned axially below the spring portion is expandable to facilitate insertion of the head of the bone anchoring element through the opening into the accommodation space and compressible to prevent removal of the head when the head is in the accommodation space.

18. The coupling assembly of claim 17, wherein the ring-shaped portion is integrally formed with the pressure element at an axial position below the spring portion.

19. The coupling assembly of claim 18, wherein the pressure element defines a hollow interior chamber for holding and clamping the head of the bone anchoring element therein.

20. The coupling assembly of claim 17, wherein the spring portion is radially compressible.

21. The coupling assembly of claim 17, wherein the second end of the spring portion is closer to the first end of the receiving part than the first end of the spring portion is to the first end of the receiving part.

22. The coupling assembly of claim 17, wherein a circumferential length of the spring portion is shorter than a circumferential length of the ring-shaped portion.

23. The coupling assembly of claim 17, wherein the spring portion is a first spring portion, and wherein the pressure element further comprises a second spring portion which extends circumferentially in a direction opposite the first direction around the central axis from a first end that is connected to yet another portion of the pressure element to a free second end.

24. A polyaxial bone anchoring device comprising the coupling assembly of claim 17 and the bone anchoring element having a shank for anchoring to a bone and the head.

25. The polyaxial bone anchoring device of claim 24, wherein when the second end of the spring portion engages the receiving part, the pressure element exerts a frictional force on the head that temporarily holds an angular position of the shank relative to the receiving part.

26. The coupling assembly of claim 17, wherein at least part of the pressure element forms a closed ring that is configured to extend uninterruptedly around an entire circumference of the pressure element.

* * * * *